United States Patent [19]

Hao et al.

[11] Patent Number: 5,502,196

[45] Date of Patent: Mar. 26, 1996

[54] PYRROLO[3,4-C]PYRROLES CONTAINING AMINE OXIDE GROUPS

[75] Inventors: Zhimin Hao, Marly; Abul Iqbal, Arconciel; Rudolf Kirchmayr, Marly, all of Switzerland

[73] Assignee: Ciba-Geigy Corporation, Tarrytown, N.Y.

[21] Appl. No.: 404,012

[22] Filed: Mar. 14, 1995

[30] Foreign Application Priority Data

Mar. 21, 1994 [CH] Switzerland .................. 843/94

[51] Int. Cl.⁶ .............................. C07D 211/10
[52] U.S. Cl. ................ 546/271; 546/101; 546/153; 546/155; 546/167; 548/453
[58] Field of Search ............... 548/453; 546/101, 546/153, 155, 167, 271

[56] References Cited

U.S. PATENT DOCUMENTS

| | | | |
|---|---|---|---|
| 4,415,685 | 11/1983 | Iqbal et al. | 524/92 |
| 4,579,949 | 4/1986 | Rochat et al. | 546/167 |
| 4,582,771 | 4/1986 | Ohta | 430/58 |
| 4,585,878 | 4/1986 | Jost et al. | 548/453 |
| 4,632,893 | 12/1986 | Rochat et al. | 430/58 |
| 4,778,889 | 10/1988 | Szczepanski | 544/211 |
| 5,378,276 | 1/1995 | Chassot et al. | 106/493 |

FOREIGN PATENT DOCUMENTS

| | | |
|---|---|---|
| 0061426 | 9/1982 | European Pat. Off. |
| 0094911 | 11/1983 | European Pat. Off. |
| 0133156 | 2/1985 | European Pat. Off. |
| 0187620 | 7/1986 | European Pat. Off. |
| 0612747 | 8/1994 | European Pat. Off. |

OTHER PUBLICATIONS

CA 100:87260q 1,4–Dioxopyrrolo[3,4–c]pyrroles. Rochat et al., pp. 79–80, 1984.
CA 105:210422b Pigment blends. Iqbal et al., pp. 76–77, 1986.
Derwent Abstract 93–137476 of JP–A–05 072 769, 1991.
Derwent Abstract 91–062038 of JP–A–03 011 357, 1989.
Derwent Abstract 90–086701 of JP–A–02 039 159, 1988.
Japan Hard copy '88 p. 22 (1988).

*Primary Examiner*—Joseph K. McKane
*Attorney, Agent, or Firm*—Michele A. Kovaleski

[57] ABSTRACT

The invention relates to pyrrolo[3,4-c]pyrroles of formula

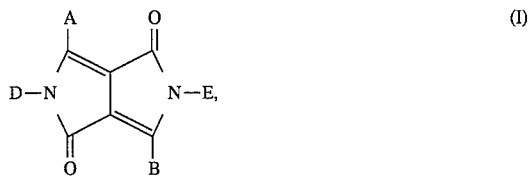

wherein A and B are each independently of the other a group of formula

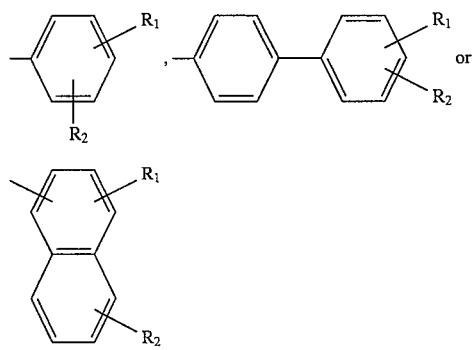

or Q, wherein Q is a 5- or 6-membered heterocyclic aromatic amine oxide radical which is unsubstituted or substituted by one, two or three $C_1$–$C_{18}$alkyl, $C_1$–$C_{18}$alkoxy or

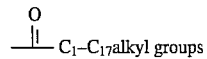 $C_1$–$C_{17}$alkyl groups and which may contain one or two fused benzene rings, $R_1$ and $R_2$ are each independently of the other hydrogen, halogen, $C_1$–$C_{18}$alkyl, $C_1$–$C_{18}$alkoxy, $C_1$–$C_{18}$alkylmercapto, —CN, —NO₂ or trifluoromethyl, D and E are each independently of the other hydrogen, $C_1$–$C_{18}$alkyl, $C_2$–$C_4$alkenyl, $C_7$–$C_{10}$aralkyl, unsubstituted phenyl or phenyl which is substituted by chloro, bromo, $C_1$–$C_6$alkyl, $C_1$–$C_4$alkoxy, trifluoromethyl or nitro, with the proviso that at least one of the sustituents A and B is an amine oxide radical Q.

These novel diketopyrrolo[3,4-c]pyrroles are suitable for use as pigments, but especially as photoconductive substances in electrophotographic photoreceptors.

4 Claims, No Drawings

PYRROLO[3,4-C]PYRROLES CONTAINING AMINE OXIDE GROUPS

The present invention relates to diketopyrrolo[3,4-c]pyrroles, to a process for their preparation and to the use thereof as pigments and, in particular, as photoconductive substances in electrophotographic photoreceptors.

Diketopyrrolo[3,4-c]pyrroles which are substituted symmetrically and asymmetrically by heteroaromatic substituents (specifically pyridyl) and the use thereof as pigments are disclosed in U.S. Pat. Nos. 4,579,949 and 4,778,899.

There have now been found novel diketopyrrolo[3,4-c]pyrroles which are substituted by heteroaromatic amine oxide radicals and which have very good pigment properties and, in addition, owing to their surprisingly high photoconductivity, are suitable for use as photoconductors in electrophotographic photoreceptors.

Accordingly, the invention relates to pyrrolo[3,4-c]pyrroles of formula

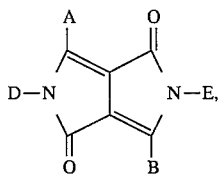  (I)

wherein A and B are each independently of the other a group of formula

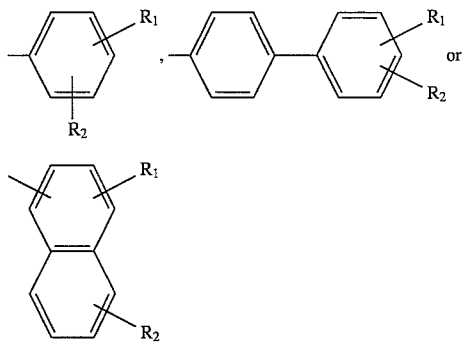

or Q, wherein Q is a 5- or 6-membered heterocyclic aromatic amine oxide radical which is unsubstituted or substituted by one, two or three $C_1$–$C_{18}$alkyl, $C_1$–$C_{18}$alkoxy or

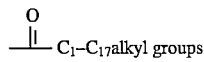 groups and which may contain one or two fused benzene rings, $R_1$ and $R_2$ are each independently of the other hydrogen, halogen, $C_1$–$C_{18}$alkyl, $C_1$–$C_{18}$alkoxy, $C_1$–$C_{18}$alkylmercapto, —CN, —$NO_2$ or trifluoromethyl, D and E are each independently of the other hydrogen, $C_1$–$C_{18}$alkyl, $C_2$–$C_4$alkenyl, $C_7$–$C_{10}$aralkyl, unsubstituted phenyl or phenyl which is substituted by chloro, bromo, $C_1$–$C_6$alkyl, $C_1$–$C_4$alkoxy, trifluoromethyl or nitro, with the proviso that at least one of the sustituents A and B is an amine oxide radical Q.

$C_1$–$C_{18}$Alkyl groups are straight-chain or branched and contain preferably 1 to 6 and, more particularly, 1 to 4, carbon atoms. Such groups are typically methyl, ethyl, n-propyl, isopropyl, n-butyl, sec-butyl, tert-butyl, pentyl, hexyl, heptyl, pctyl, nonyl, decyl, undecyl, tridecyl, hexadecyl or octadecyl.

Preferred alkoxy groups are typically methoxy, ethoxy, n-propoxy, isopropoxy, butoxy, pentoxy, hexyloxy, and also heptyloxy, octyloxy, nonyloxy, decyloxy, dodecyloxy, hexydecyloxy or octadecyloxy.

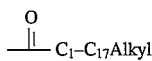

will typically be methylcarbonyl, ethylcarbonyl, propylcarbonyl, pentylcarbonyl, hexylcarbonyl, heptylcarbonyl, hendecylcarbonyl or heptadecylcarbonyl.

$C_1$–$C_{18}$Alkylmercapto will typically be methylmercapto, ethylmercapto, propylmercapto, butylmercapto, octylmercapto, decylmercapto, hexadecylmercapto or octadecylmercapto.

$C_2$–$C_4$Alkenyl is typically vinyl, allyl, methallyl or 2-butenyl.

$C_7$–$C_{10}$Aralkyl is typically 1-phenethyl, 1,1-dimethylbenzyl, benzyl which is substituted in the nucleus by methyl or ethyl or, preferably, benzyl.

Halogen substituents may conveniently be iodo, fluoro, preferably bromo and, most preferably, chloro.

Particularly interesting pyrrolo[3,4-c]pyrroles are those of formula (I) as defined above, wherein Q is a radical of formula

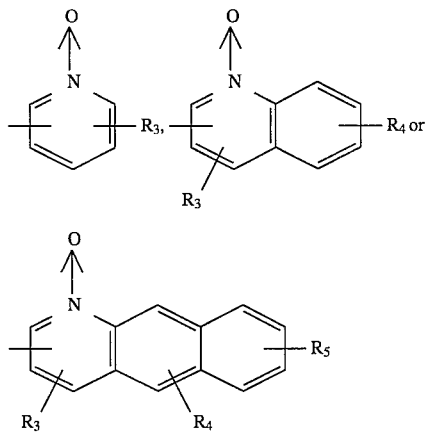

wherein $R_3$, $R_4$ and $R_5$ are each independently of the other hydrogen, $C_1$–$C_4$alkyl, $C_1$–$C_{14}$alkoxy or

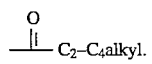

Preferred pyrrolo[3,4-c]pyrroles are those of formula

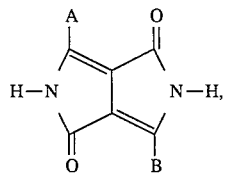  (II)

wherein A and B are each independently of the other a group of formula

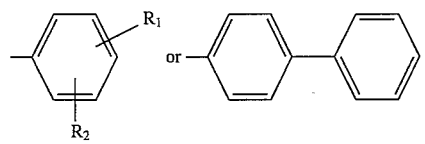

or Q, wherein $R_1$ and $R_2$ are each independently of the other hydrogen, chloro, bromo, $C_1$–$C_4$alkyl, $C_1$–$C_6$alkoxy or CN, and Q has the preferred meaning given above, especially if Q is a radical of formula

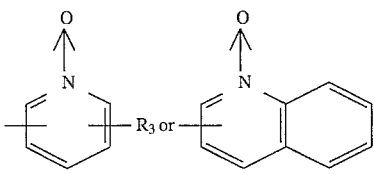

wherein $R_3$ is hydrogen or $C_1$–$C_4$alkyl.

Particularly preferred pyrrolo[3,4-c]pyrroles are those of formula

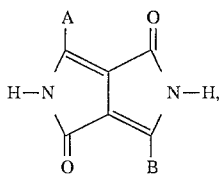

(II)

wherein A and B are each independently of the other a group of formula

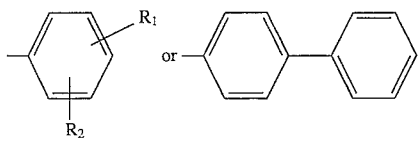

or Q, wherein $R_1$ and $R_2$ are each independently of the other hydrogen, chloro, bromo, $C_1$–$C_4$alkyl, $C_1$–$C_6$alkoxy or CN, and Q is a radical of formula

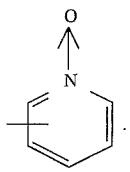

Pyrrolo[3,4-c]pyrroles of formula I can be prepared by methods analogous to standard known methods, typically a) by reacting 1 mol of a succinic acid diester of formula

(III)

with 1 mol of each of the nitriles

A—CN and B—CN, (IV) (V)

wherein R is $C_1$–$C_6$alkyl and A and B are as defined above, with the proviso that at least one of the radicals A and B must be Q, in accordance with the method described in U.S. Pat. No. 4,579,949, to give the diketopyrrolo[3,4-c]pyrrole of formula

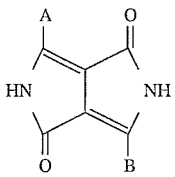

(VI)

or b) by reacting 1 mol of the pyrrolinone of formula

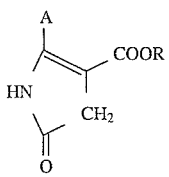

(VII)

with 1 mol of a nitrile of formula V, wherein R, A and B are as defined above, with the proviso that at least one of the substituents A and B must be Q, in accordance with the method described in U.S. Pat. No. 4,778,899, to give likewise the diketopyrrolo[3,4-c]pyrrole of formula VI.

From this latter it is possible to obtain a diketopyrrolo[3,4-c]pyrrole of formula I, wherein D and E are not hydrogen, by reacting 1 mol of a diketopyrrolo[3,4-c]pyrrole of formula VI with 1 mol of a compound containing the radicals D and E in the above significance of leaving groups with the exception of hydrogen, in accordance with the method described in U.S. Pat. No. 4,585,878.

The pyrrolo[3,4-c]pyrroles of formula I characterised by the presence of at least one aromatic amine oxide radical can also be prepared c) by oxidation, in accordance with standard known methods, of one pyrrolo[3,4-c]pyrrole containing at least one corresponding aromatic amino radical.

The compounds of formulae III, IV, V and VII and the pyrrolo[3,4-c]pyrrole containing at least one corresponding aromatic amino radical are known compounds. Any that are novel can be prepared by methods analogous to known ones.

The pyrrolo[3,4-c]pyrroles of formula I are suitable for use as pigments for colouring high-molecular weight organic material in the same manner as already described in U.S. Pat. Nos. 4,579,949, 4,778,899 and 4,585,878.

The pyrrolo[3,4-c]pyrroles of formula I are of particular interest as photoconductive substances in electrophotographic photoreceptors. Such photoreceptors consist of a photoconductive substrate and a photoconductor that is insulating in the dark but is conductive when exposed. The photoconductor can consist of one layer or of a plurality of layers. Where the photoconductor consists of a single layer, at least one photoconductive substance is dispersed in at least one binder or coated direct by evaporation onto a photoconductive substrate. A multilayer photoconductor preferably consists of at least one photoconductive layer comprising one or more than one photoconductive substance, and at least one charge-carrying layer.

Accordingly, the invention further relates to an electrophotographic photoreceptor comprising at least one conductive substrate, a photoconductive layer and a charge-carrying layer, at least one of which layers contains at least one pyrrolo[3,4-c]pyrrole of formula I and preferably at least one pyrrolo[3,4-c]pyrrole of formula II.

The conductive substrate may consist of a metal plate or foil that is untreated or pretreated by toughening and is of aluminium, zinc, magnesium, copper or an alloy of these metals. If the substrate is an aluminium sheet, the pretreatment may consist of anodic oxidation. Other suitable substrates are aluminium-coated plastic sheets as well as polymeric films having a metallised surface.

The photoconductor contains at least one pyrrolo[3,4-c]pyrrole of formula I as photoconductive compound and, as charge-carrying substances, compounds such as hydrazones, oxadiazoles, oxazoles or pyrazolines, as well as arylamines, which are dissolved in the polymeric binder. Such an arrangement permits, after prior static charging and imagewise exposure, the production of a corresponding image of charged and uncharged areas (latent image) which can be converted into a visible image by known methods of reproduction technology.

Exposure can be made with light in the visible wave range and high light sensitivities are achieved.

By virtue of their high dark resistance, the pyrrolo[3,4-c]pyrroles of formula I contribute to the maintenance of the static potential at areas that are not exposed.

If the photoconductor consists of a single layer, then said layer contains one or more than pyrrolo[3,4-c]pyrrole of formula I preferably in finely divided form, without or together with charge-carrying substances in an organic binder. The binder is preferably film-forming, insulating and adhesive. Depending on the use, the binder is soluble in organic solvents or in basic mixtures of organic solvents that may or may not contain water. Particularly suitable binders are those derived from polycondensates and polyadducts such as polyamides, polyurethanes, polyesters, epoxy resins, phenoxy resins, polyketones, polycarbonates, polyvinyl ketones, polystyrenes, polyvinyl carbazoles, polyacrylamides, polymethyl methacrylates, polyvinyl butyrate, polyvinyl chloride, polyvinyl acetate, as well as copolymers such as styrene-maleic anhydride copolymers, styrene-methacrylic acid-methacrylate copolymers or vinyl chloride-vinyl acetate copolymers.

If the photoconductor consists of a plurality of layers, then double layers merit particular interest. In this case, a photoconductive layer is first applied to the conductive substrate and a second, charge-carrying layer is then coated on to the photoconductive layer. The layers can also be applied in reverse order. One of the layers, preferably the charge carrying layer, contains at least one pyrrolo[3,4-c]pyrrole of formula I. This pyrrolo[3,4-c]pyrrole can be dissolved or finely dispersed in an organic binder. Application to the conductive substrate is conveniently made by applying a solution or dispersion of the binder/colorant mixture in an organic solvent and subsequently evaporating the solvent. The pyrrolo[3,4-c]pyrrole of formula I can also be coated on to the conductive substrate by vapour deposition.

The second layer contains one or more than one charge carrying substance, preferably dissolved or dispersed in an organic binder. Suitable charge-carrying substances embrace a wide range of aromatic, preferably nitrogen-containing, compounds such as hydrazones or aromatic amines that may contain alkylidene bridges or radicals. Such substances are typically those described in U.S. Pat. No. 4,582,771, columns 56–60, and in the publication "Japan, Hardcopy '88, Post-International Symposium in Kansa; Recent Progress in Hardcopy Materials in Electrophotography", page 22 (Osaka, JP, 23.5.88).

The invention thus also relates to the preparation of an electrophotographic photoreceptor, which comprises applying a pyrrolo[3,4-c]pyrrole of formula I to a conductive substrate with an organic binder or by vapour deposition under vacuum and subsequently coating thereon a second, charge-carrying layer containing an aromatic nitrogen-containing compound.

To enhance the physical properties of the layers, the photoconductive layer as well as the charge carrying layer may contain further additives such as levelling agents, surfactants or plasticisers.

The following Examples illustrate the invention.

Example 1: 6.90 g of sodium are stirred in 120 ml of tert-amyl alcohol at reflux temperature until the reaction is complete. After cooling to 90° C., 24.02 g of 4-cyanopyridine-N-oxide are added, followed by the dropwise addition of 20.23 g of diisopropyl succinate over 4 hours. The reaction mixture is stirred for 4 hours at 80° C. and then cooled to 30° C. A mixture of 29.56 g of hydrochloric acid and 240 ml of methanol/water (1:2) is run in and stirring is continued for a further 1 hour at room temperature. The precipitated pigment is isolated by filtration, washed with water and extracted hot with methanol. After filtration, the resultant crystals are washed with methanol and water and dried under vacuum, affording 6.80 g (21% of theory) of the compound of formula

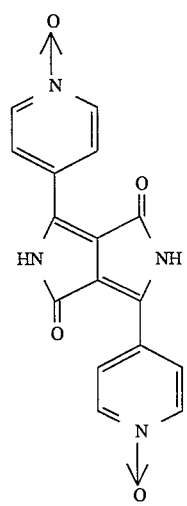

in the form of dark-red crystals with a melting point >250° C.

| Analysis | C | H | N |
|---|---|---|---|
| calcd: | 59.63% | 3.13% | 17.38% |
| found: | 59.98% | 4.00% | 17.82%. |

Example 2: 6.81 g of sodium methylate are stirred in 70 ml of methanol at reflux temperature until the reaction is complete. Then 6.05 g of 4-cyanopyridine-N-oxide are added, followed by the addition in small portions of 9.71 g of the compound of formula

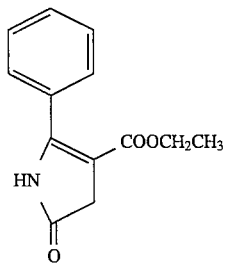

over 2 hours. The mixture is refluxed for 4 hours and then cooled to 40° C. A mixture of 12.4 g of hydrochloric acid and 140 ml of water is added dropwise and stirring is continued for a further 1 hour. The precipitated pigment is isolated by filtration, washed with water and extracted hot with methanol. After filtration, the resultant crystals are washed with methanol and then with water and dried under vacuum at 80° C., affording 3.65 g (28.4 % of theory) of a pigment of formula

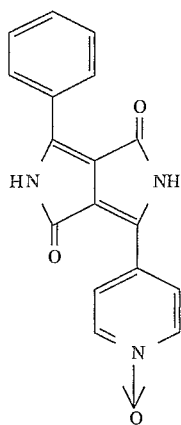

| Analysis | C | H | N |
|---|---|---|---|
| calcd: | 66.88% | 3.63% | 13.76% |
| found: | 66.02% | 3.96% | 13.46%. |

Example 3A: 5.21 g of 3-cyanopyridine are completely dissolved in 50 ml of glacial acetic acid at 40° C., with stirring. Then 9.8 ml of a 30% aqueous solution of $H_2O_2$ are added and the mixture is heated, with stirring, to 100° C. for 2 hours. Thin-layer chromatography shows that the reaction is complete. The solvent is cautiously removed by evaporation and the beige solid is treated with 25 ml of ethanol, cooled and and filtered. The residue is dried at 35° C. under vacuum, affording 3.5 g (58.3% of theory) of 3-cyanopyridine-N-oxide as a white solid with a melting point of 172°–174° C.

| Analysis | C | H | N |
|---|---|---|---|
| calcd: | 60.00% | 3.36% | 23.32% |
| found: | 59.36% | 3.43% | 23.07%. |

Example 3B: 4.18 g of sodium methylate are suspended in 35 ml of methanol (dried over a molecular sieve) under nitrogen at 60° C. Then 3.4 g of 3-cyanopyridine-N-oxide are added, followed by the addition over 1 hour in small portions of 5.78 g of the compound of formula

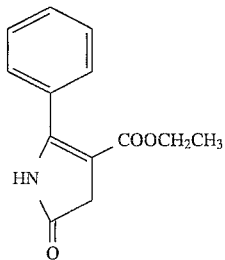

The mixture is refluxed for 5 hours, then charged to a solution of 7.4 g of hydrochloric acid in 70 ml of water. The suspension is stirred for 1 hour and filtered. The residue is washed with water and dried under vacuum at 60° C., affording 2.1 g (27.5 % of theory) of a dark-red pigment of formula

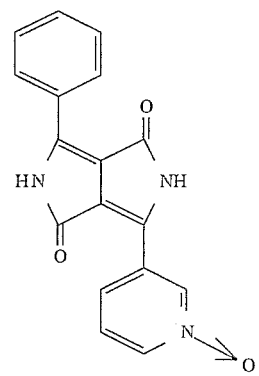

| Analysis | C | H | N |
|---|---|---|---|
| calcd: | 66.88% | 3.63% | 13.76% |
| found: | 66.24% | 3.71% | 13.60%. |

Example 4: 0.3 g of the product of Example 2 is taken up in a mixture of 10 g of xylene and 2-ethoxyethanol (2:1 in volume), containing 1.0 g of a commercially available alkyd/melamine resin (1:1 in weight). The suspension is then milled for 5 hours with glass beads and afterwards applied with an applicator rod to an aluminium plate (=charge-carrying layer). This layer is then dried at 50° C. for 3 hours. The layer thickness is c. 1 µm. A second layer consisting of a mixture of 0.6 g of a hydrazone of formula

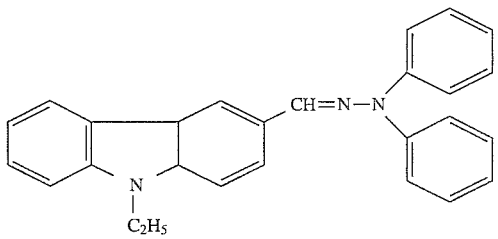

and 0.9 g of the polyacrylate varnish ®Lucite 41 in 11 g of methyl ethyl ketone is then applied and dried at 50° C. for 15 hours. The layer thickness is 1–15 µm. This photoreceptor is distinguished by unexpectedly high light sensitivity and charging properties.

Example 5: The product of Example 2 is coated by vapour deposition at a rate of 5 Å/sec under a vacuum of $10^{-6}$ mbar on to an aluminium substrate. The layer thickness is c. 1000 Å. A second layer consisting of a mixture of 0.6 g of a hydrazone of formula

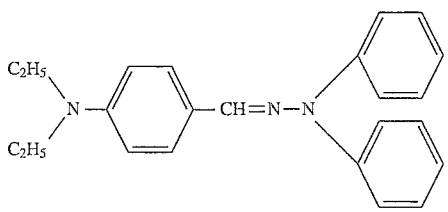

and 0.6 g of polycarbonate (®Makrolon, DuPont) in 10 g of tetrahydrofuran, is afterwards applied and dried at 50° C. for 6 hours. The layer thickness is c. 15 µm. This photoreceptor is also distinguished by unexpectedly high light sensitivity.

What is claimed is:

1. A pyrrolo[3,4-c]pyrrole of formula

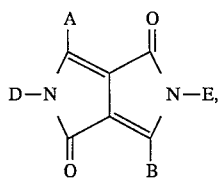

(I)

wherein A and B are each independently of the other a group of formula

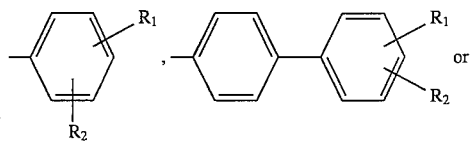

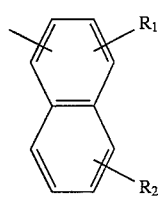

or Q, wherein Q is a 5- or 6-membered heterocyclic aromatic amine oxide radical which is unsubstituted or substituted by one, two or three $C_1$–$C_{18}$alkyl, $C_1$–$C_{18}$alkoxy or

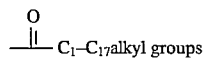

groups and which may contain one or two fused benzene rings, $R_1$ and $R_2$ are each independently of the other hydrogen, halogen, $C_1$–$C_{18}$alkyl, $C_1$–$C_{18}$alkoxy, $C_1$–$C_{18}$alkylmercapto, —CN, —NO$_2$ or trifluoromethyl, D and E are each independently of the other hydrogen, $C_1$–$C_{18}$alkyl, $C_2$–$C_4$alkenyl, $C_7$–$C_{10}$aralkyl, unsubstituted phenyl or phenyl which is substituted by chloro, bromo, $C_1$–$C_6$alkyl, $C_1$–$C_4$alkoxy, trifluoromethyl or nitro, with the proviso that at least one of the substituents A and B is an amine oxide radical Q.

2. A pyrrolo[3,4-c]pyrrole according to claim 1, wherein Q is a radical of formula

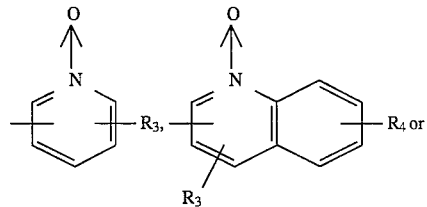

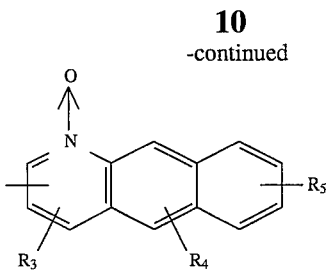

wherein $R_3$, $R_4$ and $R_5$ are each independently of the other hydrogen, $C_1$–$C_4$alkyl, $C_1$–$C_4$alkoxy or

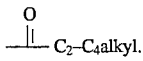

3. A pyrrolo[3,4-c]pyrrole according to claim 2, of formula

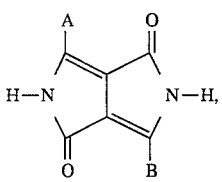

(II)

wherein A and B are each independently of the other a group of formula

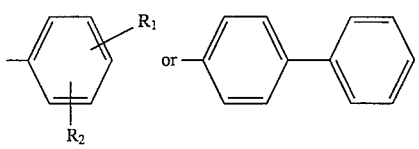

or Q, wherein $R_1$ and $R_2$ are each independently of the other hydrogen, chloro, bromo, $C_1$–$C_4$alkyl, $C_1$–$C_6$alkoxy or CN.

4. A pyrrolo[3,4-c]pyrrole according to claim 3, wherein Q is a radical of formula

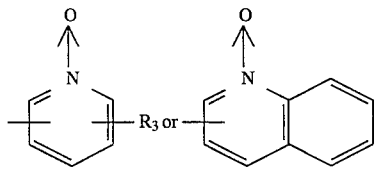

wherein $R_3$ is hydrogen or $C_1$–$C_4$alkyl.

* * * * *